(12) United States Patent
Masuda et al.

(10) Patent No.: US 11,448,782 B2
(45) Date of Patent: Sep. 20, 2022

(54) RADIATION IMAGING APPARATUS, RADIATION IMAGING SYSTEM, AND CONTROL METHOD FOR RADIATION IMAGING SYSTEM

(71) Applicant: CANON KABUSHIKI KAISHA, Tokyo (JP)

(72) Inventors: Rikuto Masuda, Kanagawa (JP); Taro Hiroike, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 28 days.

(21) Appl. No.: 17/095,608

(22) Filed: Nov. 11, 2020

(65) Prior Publication Data

US 2021/0149064 A1 May 20, 2021

(30) Foreign Application Priority Data

Nov. 19, 2019 (JP) .............................. JP2019-209002

(51) Int. Cl.
  *G01T 1/29* (2006.01)
  *G01T 1/17* (2006.01)
  *A61B 6/00* (2006.01)

(52) U.S. Cl.
  CPC .............. *G01T 1/2978* (2013.01); *G01T 1/17* (2013.01); *A61B 6/461* (2013.01); *A61B 6/52* (2013.01)

(58) Field of Classification Search
  CPC .......... G01T 1/2978; A61B 6/461; A61B 6/52
  See application file for complete search history.

(56) References Cited

U.S. PATENT DOCUMENTS

| | | | |
|---|---|---|---|
| 2008/0107234 A1* | 5/2008 | Amitani ................. | A61B 6/548 378/98 |
| 2011/0211672 A1* | 9/2011 | Kuwabara ............ | A61B 6/4494 378/62 |
| 2016/0249873 A1* | 9/2016 | Kawanishi ............. | A61B 6/467 378/98.5 |
| 2018/0125441 A1* | 5/2018 | Arima ................. | A61B 6/5205 |

(Continued)

FOREIGN PATENT DOCUMENTS

| | | |
|---|---|---|
| JP | 2002-171265 A | 6/2002 |
| JP | 2011-235093 A | 11/2011 |

(Continued)

*Primary Examiner* — Blake C Riddick
(74) *Attorney, Agent, or Firm* — Canon U.S.A., Inc. IP Division

(57) ABSTRACT

A plurality of radiation imaging systems each comprises a radiation imaging apparatus and a control apparatus. The radiation imaging apparatus comprises a communication unit configured to transmit apparatus information for identifying an apparatus to the control apparatus of the radiation imaging system as a movement destination, a display unit configured to display a name and a state of the radiation imaging apparatus, and a display control unit configured to control the display unit. The control apparatus comprises a search unit configured to search for apparatus information usable in the radiation imaging system as the movement destination based on the transmitted apparatus information, a decision unit configured to decide, based on a result of the search, a name to be assigned to the radiation imaging apparatus, and a communication unit configured to transmit the name to the radiation imaging apparatus.

20 Claims, 14 Drawing Sheets

(56) References Cited

U.S. PATENT DOCUMENTS

| | | | | |
|---|---|---|---|---|
| 2018/0246225 A1* | 8/2018 | Tanaka | ................. | G01T 1/17 |
| 2018/0270369 A1* | 9/2018 | Haraguchi | ......... | H04N 1/32374 |

FOREIGN PATENT DOCUMENTS

| JP | 2013-240018 A | 11/2013 |
|---|---|---|
| JP | 2014-138350 A | 7/2014 |
| JP | 2015-177988 A | 10/2015 |

* cited by examiner

F I G. 4

RADIATION IMAGING SYSTEM A

| NAME | STATE | SIZE | STATE | CONNECTION | CHARGE AMOUNT |
|---|---|---|---|---|---|
| Sys1-A | IN USE | HALF | GOOD | WIRELESS | 83% |
| Sys1-B | IN USE | FULL | GOOD | WIRED | 76% |
| Sys1-C | NOT IN USE | | | | |
| Sys1-D | NOT IN USE | | | | |
| Sys1-E | NOT IN USE | | | | |

RADIATION IMAGING SYSTEM B

| NAME | STATE | SIZE | STATE | COOPERATING TERMINAL | CHARGE AMOUNT |
|---|---|---|---|---|---|
| Sys2-A | NOT IN USE | | | | |
| Sys2-B | IN USE | HALF | GOOD | WIRELESS | 75% |
| Sys2-C | IN USE | HALF | GOOD | WIRELESS | 75% |
| Sys2-D | NOT IN USE | | | | |
| Sys2-E | IN USE | FULL | GOOD | WIRELESS | 75% |

FIG. 8A

☐ MANUAL　　■ SERIAL NUMBER
■ AUTOMATIC　☐ ALPHABET
　　　　　　　☐ ORIGINAL

| RADIATION IMAGING SYSTEM A | | |
|---|---|---|
| NAME | STATE | SIZE |
| Xray system1-001 | IN USE | HALF |
| Xray system1-002 | IN USE | HALF |
| Xray system1-003 | NOT IN USE | |
| Xray system1-004 | NOT IN USE | |
| Xray system1-005 | NOT IN USE | |

FIG. 8B

☐ MANUAL　　☐ SERIAL NUMBER
■ AUTOMATIC　■ ALPHABET
　　　　　　　☐ ORIGINAL

| RADIATION IMAGING SYSTEM A | | |
|---|---|---|
| NAME | STATE | SIZE |
| Xray system1-A | IN USE | HALF |
| Xray system1-B | IN USE | HALF |
| Xray system1-C | NOT IN USE | |
| Xray system1-D | NOT IN USE | |
| Xray system1-E | NOT IN USE | |

FIG. 8C

☐ MANUAL　　☐ SERIAL NUMBER
■ AUTOMATIC　☐ ALPHABET
　　　　　　　■ ORIGINAL

| RADIATION IMAGING SYSTEM A | | |
|---|---|---|
| NAME | STATE | SIZE |
| Xray system1-alpha | IN USE | HALF |
| Xray system1-beta | IN USE | HALF |
| Xray system1-gamma | NOT IN USE | |
| Xray system1-delta | NOT IN USE | |
| Xray system1-epsilon | NOT IN USE | |

F I G. 9

| RADIATION IMAGING SYSTEM A | | | | | |
|---|---|---|---|---|---|
| NAME | SIZE | STATE | STATE | CONNECTION | CHARGE AMOUNT |
| Sys1-A | HALF | IN USE | GOOD | WIRELESS | 83% |
| Sys1-B | HALF | NOT IN USE | | | |
| Sys1-C | FULL | IN USE | GOOD | WIRED | 76% |
| Sys1-D | FULL | NOT IN USE | | | |
| Sys1-E | LARGE QUARTER | IN USE | GOOD | WIRED | 55% |
| Sys1-F | LARGE QUARTER | NOT IN USE | | | |

RADIATION IMAGING APPARATUS, RADIATION IMAGING SYSTEM, AND CONTROL METHOD FOR RADIATION IMAGING SYSTEM

BACKGROUND OF THE DISCLOSURE

Field of the Disclosure

The present invention relates to a radiation imaging apparatus used for radiation imaging in the medical field, and a radiation imaging system using the radiation imaging apparatus, and a control method for the radiation imaging system.

Description of the Related Art

In recent years, as an imaging apparatus used for medical imaging diagnosis or non-destructive inspection by X-rays or the like, a radiation imaging apparatus that uses a flat panel detector (to be referred to as an "FPD" hereinafter) made of a semiconductor material has been used. This FPD includes a pixel array in which a plurality of pixels each for converting radiation into an electrical signal are arrayed in a two-dimensional matrix, and converts, into digital data, an electrical signal obtained from the pixel array, thereby outputting a digital radiation image for one image (frame). Such radiation imaging apparatus is used as a digital imaging apparatus for still image capturing such as general imaging or moving image capturing such as fluoroscopic imaging in, for example, medical imaging diagnosis.

This radiation imaging apparatus is wireless to improve portability, and does not limit a radiation imaging system to be used, and one radiation imaging apparatus can thus be used in various radiation imaging systems.

Japanese Patent Laid-Open No. 2011-235093 discloses a system in which each radiation imaging apparatus is assigned with a different name as an index identifiable by a user and it is possible to confirm the state of each radiation imaging apparatus. Japanese Patent Laid-Open No. 2015-177988 discloses a technique of giving a label to each radiation imaging apparatus, thereby making it possible to confirm a radiation imaging apparatus to be used.

However, assigning a different name to each radiation imaging apparatus is a cumbersome work. In addition, if a radiation imaging apparatus is moved and used among a plurality of radiation imaging systems, settings of a control apparatus in a radiation imaging system is confirmed as a moving destination to determine whether cooperation between the radiation imaging apparatus and the control apparatus has been performed, and it may take time for an operator to perform a work.

SUMMARY OF THE DISCLOSURE

According to one aspect of the embodiments, there is provided a plurality of radiation imaging systems each comprising a radiation imaging apparatus configured to detect radiation and generate radiation image data and a control apparatus configured to communicate with the radiation imaging apparatus, wherein the radiation imaging apparatus comprises a communication unit configured to transmit apparatus information for identifying an apparatus to the control apparatus of the radiation imaging system as a movement destination, a display unit configured to display a name of the radiation imaging apparatus and a state of the radiation imaging apparatus, and a display control unit configured to control the display of the display unit, wherein the control apparatus comprises a search unit configured to search for apparatus information usable in the radiation imaging system as the movement destination based on the transmitted apparatus information, a decision unit configured to decide, based on a result of the search by the search unit, a name to be assigned to the radiation imaging apparatus, and a communication unit configured to transmit the name decided by the decision unit to the radiation imaging apparatus, and wherein the display control unit controls the display of the display unit based on the name decided by the decision unit and received from the control apparatus.

According to another aspect of the present invention, there is provided a radiation imaging apparatus for detecting radiation and generating radiation image data, comprising: a communication unit configured to transmit apparatus information for identifying an apparatus to a control apparatus of a radiation imaging system as a movement destination; a display unit configured to display a name of the radiation imaging apparatus and a state of the radiation imaging apparatus; and a display control unit configured to control the display of the display unit, wherein the control apparatus searches for apparatus information usable in the radiation imaging system as the movement destination based on the apparatus information, and decides, based on a result of the search, a name to be assigned to the radiation imaging apparatus, and the display control unit controls the display of the display unit based on the name decided by the control apparatus.

According to still another aspect of the present invention, there is provided a control method for a plurality of radiation imaging systems each comprising a radiation imaging apparatus configured to detect radiation and generate radiation image data and a control apparatus configured to communicate with the radiation imaging apparatus, the method comprising: in the radiation imaging apparatus, transmitting apparatus information for identifying an apparatus to the control apparatus of the radiation imaging system as a movement destination, displaying, on a display unit, a name of the radiation imaging apparatus and a state of the radiation imaging apparatus, and controlling the display of the display unit; in the control apparatus, searching for apparatus information usable in the radiation imaging system as the movement destination based on the transmitted apparatus information, deciding, based on a result of the search, a name to be assigned to the radiation imaging apparatus, and transmitting the name decided in the deciding to the radiation imaging apparatus; and in the radiation imaging apparatus, controlling the display of the display unit based on the name received from the control apparatus.

Further features of the present invention will become apparent from the following description of exemplary embodiments (with reference to the attached drawings).

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 4 is a view showing an example of display of lists of radiation imaging apparatuses during cooperation;

FIGS. 8A to 8C are views showing examples of display of a list for automatically assigning names of radiation imaging apparatuses;

FIG. 9 is a view showing an example of display of a list of radiation imaging apparatuses during cooperation in accordance with sizes;

DESCRIPTION OF THE EMBODIMENTS

Figure 1:
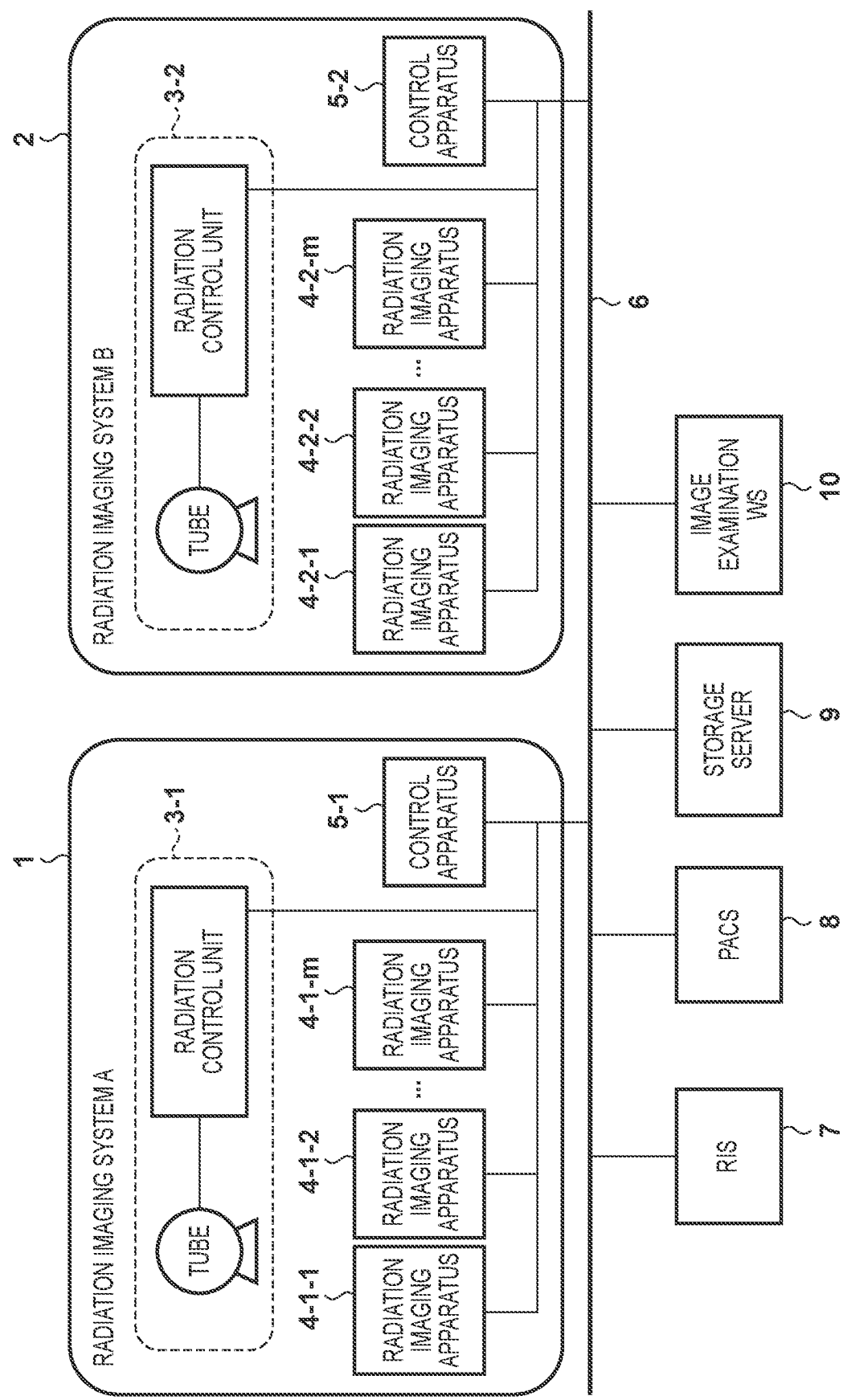
FIG. 1 is a view showing the schematic arrangement of radiation imaging systems according to the first embodiment.

Hereinafter, embodiments will be described in detail with reference to the attached drawings. Note, the following embodiments are not intended to limit the scope of the claimed invention. Multiple features are described in the embodiments, but limitation is not made an invention that requires all such features, and multiple such features may be combined as appropriate. Furthermore, in the attached drawings, the same reference numerals are given to the same or similar configurations, and redundant description thereof is omitted.

Radiation according to the embodiments of the present invention can include not only α-rays, β-rays, and γ-rays that are beams generated by particles (including photons) emitted by radioactive decay but also beams having equal or more energy, for example, X-rays, particle rays, and cosmic rays.

First Embodiment

FIG. 1 is a view showing the schematic arrangement of radiation imaging systems according to the first embodiment of the present invention. Each of a plurality of radiation imaging systems A and B includes a radiation imaging apparatus that detects radiation and generates radiation image data, and a control apparatus that can communicate with the radiation imaging apparatus. A radiation imaging system A 1 and a radiation imaging system B 2 are systems each including a radiation generating apparatus 3-1 or 3-2 formed by a radiation control unit and a tube, radiation imaging apparatuses 4-1-1 to 4-1-$m$ or 4-2-1 to 4-2-$m$, and a control apparatus 5-1 or 5-2.

The control apparatus 5-1 or 5-2 can communicate with RIS 7 (Radiology Information Systems) and a PACS 8 (Picture Archiving and Communication System) via a communication path 6. Furthermore, the control apparatus 5-1 or 5-2 of the radiation imaging system can communicate with a storage server 9 and an image examination workstation 10 via the communication path 6.

The communication path 6 is not limited to an in-hospital network, and the RIS 7 and the PACS 8 may be connected to an external cloud service or the like. In each of the radiation imaging system A 1 and the radiation imaging system B 2, one or more radiation generating apparatuses 3-1 or 3-2, one or more radiation imaging apparatuses 4-1-1 to 4-1-$m$ or 4-2-1 to 4-2-$m$, and one or more control apparatuses 5-1 or 5-2 are provided. Especially, each radiation imaging system includes one or more radiation imaging apparatuses and one control apparatus.

In the radiation imaging system A 1, the control apparatus 5-1 can be connected to the plurality of radiation imaging apparatuses 4-1-1 to 4-1-$m$ and cooperate with them. In the radiation imaging system B 2, the control apparatus 5-2 can be connected to the plurality of radiation imaging apparatuses 4-2-1 to 4-2-$m$ and cooperate with them. Connection between the control apparatus and each radiation imaging apparatus is established by, for example, wireless LAN communication complying with the IEEE802.11 standard or wired communication such as Ethernet®. Wireless LAN communication may be so-called infrastructure mode communication in which one of a wireless LAN access point (not shown), the radiation imaging apparatus, and the control apparatus, which are connected to the communication path 6, executes an access point operation to perform communication. Alternatively, wireless LAN communication may be ad hoc mode communication in which the radiation imaging apparatus and the control apparatus directly communicate with each other. The communication path 6 is not limited to wireless communication, and wired communication such as Ethernet® may be possible. The control apparatus 5-1 or 5-2 is provided with a display unit, and can display the state (for example, a power-saving standby state or an imaging preparation completion state) of the connectable radiation imaging apparatus.

The control apparatus 5-1 or 5-2 can control the radiation imaging apparatus during cooperation by an operation from the control apparatus. A radiation image obtained by irradiating the radiation imaging apparatus with radiation is transferred to the cooperative control apparatus 5-1 or 5-2, and is then displayed on the display unit of the control apparatus 5-1 or 5-2. An operator can confirm the radiation image displayed on the display unit of the control apparatus 5-1 or 5-2 after imaging.

The control apparatus 5-1 or 5-2 associates imaging order information received from the RIS 7 with the radiation image after imaging, and outputs, via the communication path 6, the radiation image to the storage server 9 that saves an image and the image examination workstation 10 for executing image processing and the like to generate a final image to be provided for diagnosis.

The control apparatus 5-1 or 5-2 may be a stationary terminal such as a desktop PC installed in a radiation room, or an embedded terminal incorporated in a mobile radiation vehicle. Furthermore, the control apparatus 5-1 or 5-2 may be a portable terminal such as a tablet PC or a smartphone of each radiologist. Especially, the portable terminal is readily carried, and a radiation generating apparatus used for CR (Computed Radiography) or a film is also used intact and upgraded to DR (Digital Radiography), thereby making it possible to suppress the initial investment. In addition, the portable terminal is useful since it can be used for emergency medical care at a disaster site in combination with a portable radiation generating apparatus that can readily be carried.

Figure 2:
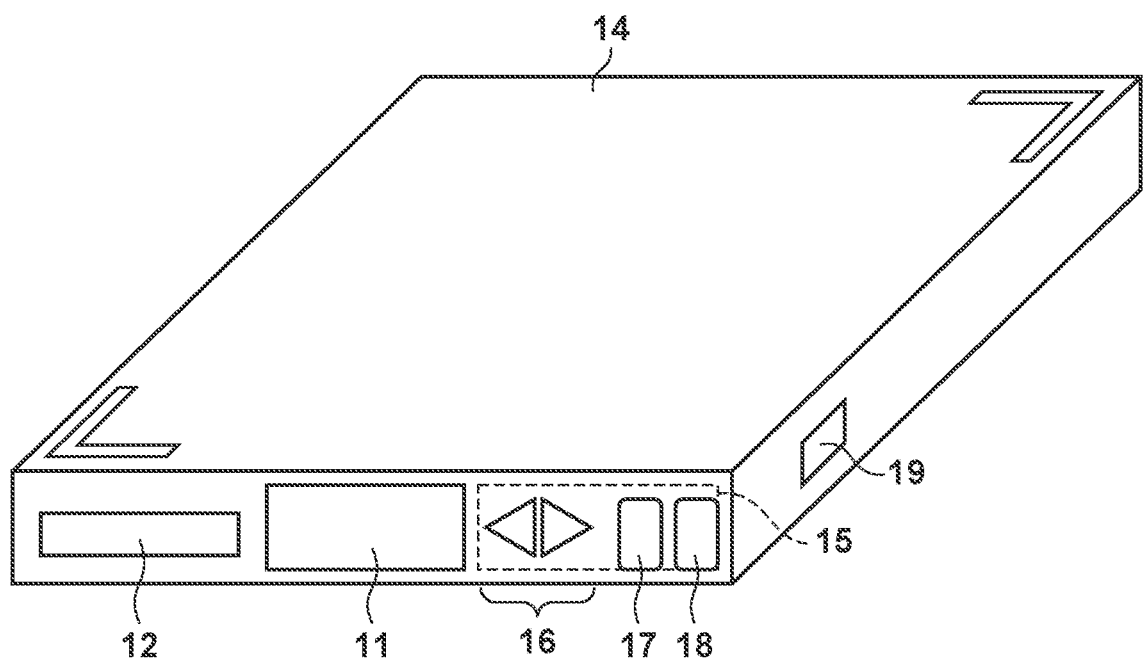
FIG. 2 is a view showing the outer appearance of a radiation imaging apparatus.

FIG. 2 is a view showing the outer appearance of each of the radiation imaging apparatuses 4-1-1 to 4-1-*m* and 4-2-1 to 4-2-*m* according to this embodiment, and is a schematic view particularly showing a portion related to an interface. As shown in FIG. 2, on the surface of each of the radiation imaging apparatuses 4-1-1 to 4-1-*m* and 4-2-1 to 4-2-*m*, a display unit 11, an external connection interface 12, an operation unit 15, and a loudspeaker 19 are provided. Each of the radiation imaging apparatuses 4-1-1 to 4-1-*m* and 4-2-1 to 4-2-*m* includes a radiation detector (not shown in FIG. 2) in its housing.

The display unit 11 has a function of displaying the state of the radiation imaging apparatus, the name of itself registered in the radiation imaging apparatus, information concerning a captured image, and the like. As the display unit 11, a display such as an LCD or OLED can be used, and an LED or the like can also be used to display the state of the radiation imaging apparatus. One display unit 11 is provided on the side surface of the radiation imaging apparatus in FIG. 2. However, the display unit 11 can be provided at a position different from a region, irradiated with radiation, of a radiation incident surface 14, and the number of arranged display units 11 is not limited to one.

The external connection interface 12 is an interface for connecting the radiation imaging apparatus and an external apparatus. For example, the external connection interface 12 is connected to the control apparatus 5-1 or 5-2 by a dedicated cable or the like, and is used to output radiation image data and input various control signals. The external connection interface 12 is connected to a cable connected to a dedicated power supply or the like to be able to externally receive power for the operation of the radiation imaging apparatus.

The operation unit 15 includes a button, dial, slide switch, touch sensor, and touch pad. The operation unit 15 is an input interface for performing various operations of the radiation imaging apparatus, and has a function of accepting an instruction from the operator. In this embodiment, four buttons of cursor buttons 16, a confirmation/reset button 17, and a power button 18 are arranged.

When the power button 18 is pressed, the ON/OFF state of the power supply of the radiation imaging apparatus is controlled. In accordance with the state of an imaging unit when the confirmation/reset button 17 is pressed, the operation of the radiation imaging apparatus is changed. Since the state of the radiation imaging apparatus is displayed on the display unit 11, when the confirmation/reset button 17 is arranged alongside the display unit 11, an operation is readily performed while viewing the display unit 11. The display unit 11 can be implemented by a touch panel, thereby implementing the function of the power button 18 or the confirmation/reset button 17 in accordance with a touch operation on the display unit 11.

The loudspeaker 19 notifies the user of the operation and state of the radiation imaging apparatus. In one embodiment, the loudspeaker 19 and the above-described display unit 11, external connection interface 12, and operation unit 15 have waterproof structures.

Figure 3:
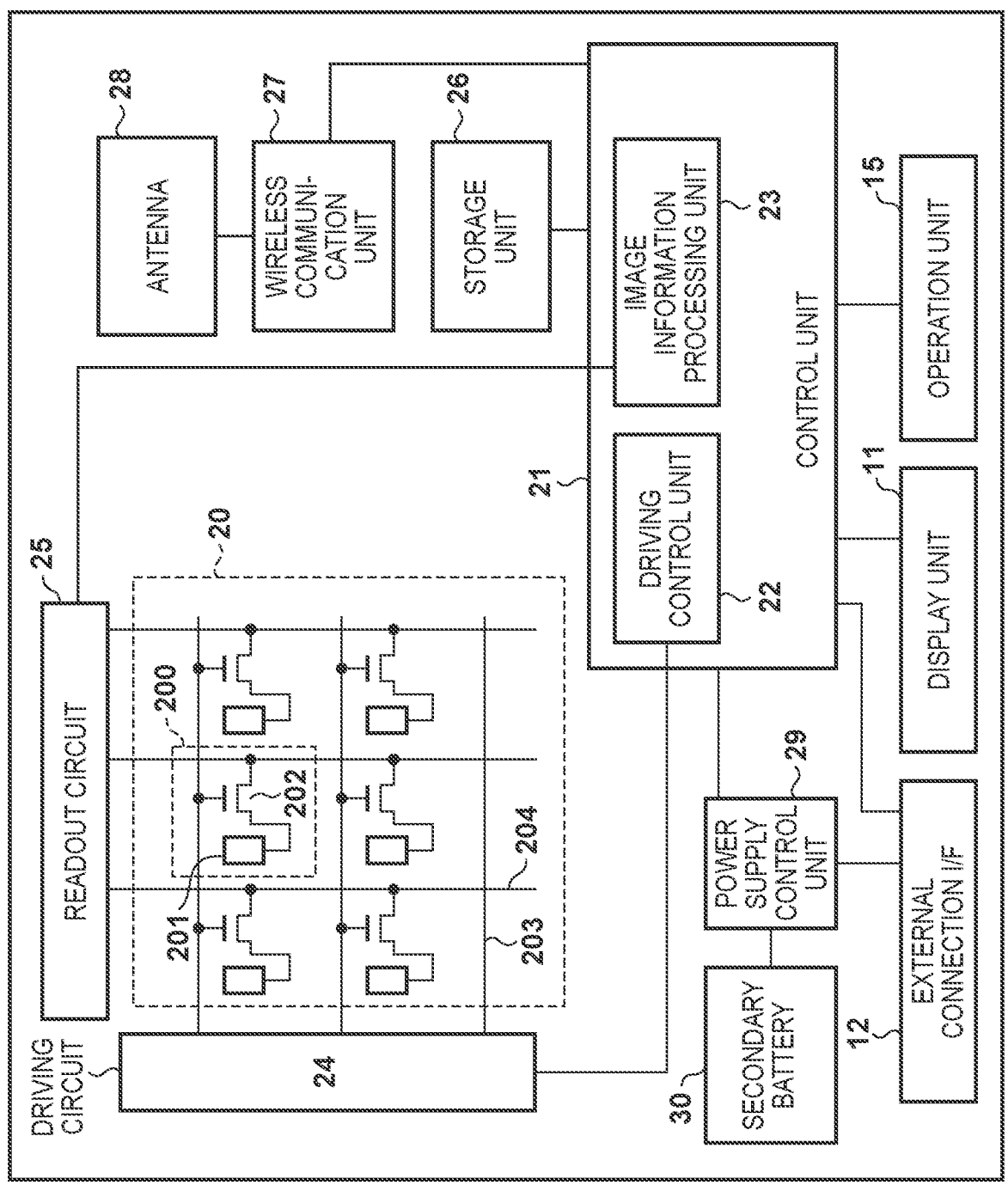
FIG. 3 is a block diagram showing an example of the arrangement of the radiation imaging apparatus.

FIG. 3 is a block diagram showing an example of the arrangement of each of the radiation imaging apparatuses 4-1-1 to 4-1-*m* and 4-2-1 to 4-2-*m* according to this embodiment. A control unit 21 controls the overall operation of the radiation imaging apparatus, and is provided with a driving control unit 22 and an image information processing unit 23. The control unit 21 functions as a display control unit that controls display of the display unit 11.

The driving control unit 22 has a function of selecting (driving) a switch element arranged in a radiation detector 20. The radiation detector 20 has a structure in which pixels 200 each including a photoelectric converting element 201 formed by a semiconductor are arrayed in a two-dimensional matrix. Each pixel 200 includes a switch element 202 and the photoelectric converting element 201, and is covered with a scintillator (not shown). The scintillator is excited based on irradiated radiation, thereby generating visible light. The photoelectric converting element 201 can convert the visible light into an electrical signal, and the pixel 200 can convert radiation into an electrical signal. Note that the arrangement of the pixel 200 is not limited to this, and a direct conversion type pixel 200 that directly converts radiation into visible light without intervention of the scintillator may be adopted.

When driving the radiation detector 20, a driving circuit 24 selects, in accordance with a control signal from the driving control unit 22, a row or a column to drive among the plurality of pixels forming the radiation detector 20.

The driving circuit 24 selects the pixels 200 on a given row via a driving wiring line 203 by a driving signal. Then, the switch elements 202 of the pixels 200 on the selected row are sequentially turned on, and image signals (charges) accumulated in the photoelectric converting elements 201 of the pixels 200 on the selected row are output to signal wiring lines 204 connected to the respective pixels 200.

Each signal wiring line 204 is connected to the image information processing unit 23 via a readout circuit 25. The readout circuit 25 includes an amplifier IC and an analog-digital converter (ADC). The amplifier IC has a function of sequentially reading out the image signals output to the signal wiring lines 204 and amplifying them. The analog-digital converter (ADC) is a unit for converting, into digital signals, the analog image signals read out by the amplifier IC. The image information processing unit 23 receives the digitally converted radiation image data.

The image information processing unit 23 performs various kinds of processes for the input radiation image data. The processes performed here can include, for example, defect correction of correcting a defect of an image, offset correction of correcting offset data of an image, and noise reduction processing of reducing various kinds of noise. Note that the image information processing unit 23 need not perform all the processes for generating a diagnostic image, and the control apparatus 5-1 or 5-2 can perform some of the processes.

Offset correction is processing of subtracting unnecessary data such as a dark current component generated during accumulation of a radiation image, and is performed by subtracting, from radiation image data acquired while radiation irradiation is performed, image data for offset correction acquired while no radiation irradiation is performed. Gain correction is a kind of processing of correcting an image error caused by individual characteristic differences of the pixels arrayed in a two-dimensional matrix, and is performed to correct a gain difference for each pixel based on gain correction information data obtained by performing irradiation with a uniform dose in a state in which there is no object.

The image information processing unit 23 determines whether the captured radiation image satisfies a predetermined standard. That is, the image information processing unit 23 functions as a determination unit for determining whether the radiation image satisfies the predetermined standard. Whether the radiation image satisfies the predetermined standard is determined based on whether the radiation image is an image at a level sufficiently usable for a purpose such as diagnosis. Determination performed by the image information processing unit 23 includes a plurality of determination items. Each determination item that can be executed by the image information processing unit 23 will be described below.

Quality determination of the radiation image includes positioning determination of determining whether a part to be imaged is included. By performing positioning determination, the image information processing unit 23 determines, based on the captured radiation image, whether the relative position between the part to be imaged and the radiation imaging apparatus is appropriate. Quality determination of the radiation image includes determination of excessive/insufficient dose based on the magnitudes of the pixel values of the radiation image, body movement detection of detecting the movement of an object during imaging, detection of misalignment of grids, determination of front-back false recognition of the radiation imaging apparatus 100, and determination of imaging at an inappropriate timing. The image information processing unit 23 executes the determination item selected from the plurality of determination items.

Since an excessive/insufficient dose is determined based on the magnitudes of the pixel values of the radiation image, the image information processing unit 23 performs level determination. Level determination is processing executed by performing statistical processing for luminance data of the entire image, and comparing the maximum and minimum values of luminance with respective thresholds. In level determination, if the number of pixels exceeding the threshold exceeds a set predetermined range, it is determined that an image failure may have occurred.

Body movement detection (or blurring detection) is processing executed by detecting a shift amount (edge component) in a given direction of the radiation image data. The image information processing unit 23 confirms whether a structure on a line in the image has a strong component in a specific direction, and determines the presence/absence of body movement. The presence/absence of body movement can be determined since most of radiation imaging operations are performed within a very short irradiation time (for example, several msec to 1 sec) and thus a shift amount generated during this time is assumed to be in one direction. At this time, since an edge component in the image influences a result as line segment information in the specific direction, edge detection is performed or the like in the image and select a region for body movement detection. The detected region is divided into small regions to support the assumption that the body movement is in one direction, and determination is performed for each divided small region. Note that in addition to the above-described method, various methods such as a method of detecting a feature amount along with body movement by analyzing a signal component obtained by frequency analysis for the radiation image can be applied to body movement detection in accordance with a part to be imaged and a technique. Furthermore, to shorten the processing time, reduced radiation image data may be processed.

A storage unit 26 saves, in association with each other, imaging information and the radiation image data processed by the image information processing unit 23. The storage unit 26 also saves imaging unit information. A nonvolatile memory such as a flash memory is used as the storage unit 26. The imaging information includes information concerning an imaged patient, information concerning a radiographer, information concerning an imaged part, information concerning the imaging date/time, and information of a unique ID or the like for identifying an image. If imaging is performed in an imaging mode in which the radiation imaging apparatus detects a radiation irradiation start to start imaging, the imaging information also includes information used for detection determination of radiation. The imaging unit information includes information of the name of the radiation imaging apparatus (imaging unit), a sensor size, a connection method (wireless, wired, or the like), and the like. The storage unit 26 can store one or a plurality of pieces of information among the pieces of imaging unit information in association with the radiation image data. The storage unit 26 may further save defect information to be used for image correction, and gain information for performing gain correction, or save the operation history of the radiation imaging apparatus.

A wireless communication unit 27 transmits the radiation image data and imaging information saved in the storage unit 26 to the control apparatus 5-1 or 5-2. The wireless communication unit 27 is connected to an antenna 28, and includes a circuit that transmits/receives radio waves via the antenna 28. The wireless communication unit 27 may transmit, to the control apparatus, the radiation image data processed by the image information processing unit 23. At this time, the wireless communication unit 27 may save the radiation image data in the storage unit 26 while transmitting it. Transmission to the control apparatus may be performed by wired communication via the external connection interface (described as an external connection I/F in FIG. 3) 12. The wireless communication unit 27 functions as a communication unit that transmits apparatus information for identifying an apparatus to the control apparatus of the radiation imaging system as a movement destination. The apparatus information is information including the name of the radiation imaging apparatus or a name set depending on the size (imageable size) of the radiation imaging apparatus.

A power supply control unit 29 is a unit for controlling the driving power supply of the radiation imaging apparatus, and receives power supplied from a secondary battery 30 and the external connection interface 12, generates various kinds of power for driving of the radiation imaging apparatus, and supplies the generated power to each unit. Furthermore, the power supply control unit 29 controls charge of the secondary battery 30.

Cooperation between the radiation imaging apparatus and the control apparatus will be described next. Referring to FIG. 1, the plurality of radiation imaging apparatuses 4-1-1 to 4-1-*m* and the control apparatus 5-1 are communicably connected, and communication between them can be either wired or wireless. Furthermore, the plurality of radiation imaging apparatuses 4-2-1 to 4-2-*m* and the control apparatus 5-2 are communicably connected, and communication between them can be either wired or wireless. The control apparatus can bring (cooperate with) the plurality of radiation imaging apparatuses under its control. That is, a state in which the radiation imaging apparatuses and the control apparatus cooperate with each other is a state in which the control apparatus causes each radiation imaging apparatus to perform an imaging operation based on a control instruction from the control apparatus, and a state in which the radiation imaging apparatuses are occupied by the control apparatus. With respect to a cooperation cancellation method, transmission/reception of a cancellation command between a plurality of control apparatuses or deterioration of the communication state with the radiation imaging apparatus may be considered. However, the present invention is not limited to the use of either of the methods.

Before the operation of the radiation imaging system, cooperation between the control apparatus and one or more radiation imaging apparatuses is performed. At this time, a list that makes it possible to identify each radiation imaging apparatus by a name (identification information) assigned to each radiation imaging apparatus is displayed on the display unit of the control apparatus for each radiation imaging system, as shown in FIG. 4. The display of the lists is merely an example but the present invention is not limited to this. In each list, a unique number or abbreviation as identification information, the size of each radiation imaging apparatus, a connection state, and the like are displayed. This name can be set by the control apparatus, and any name can be set. However, in one embodiment, a name that makes it possible to distinguish the radiation imaging system is set. For example, as shown in FIG. 4, if there are the radiation imaging systems A and B, the name of the radiation imaging apparatus used in the radiation imaging system A is set to Sys1-A or the like, and the name of the radiation imaging apparatus used in the radiation imaging system B is set to Sys2-A or the like. A description will be provided later by assuming that a name that makes it possible to distinguish the radiation imaging system is set.

Figure 5A:
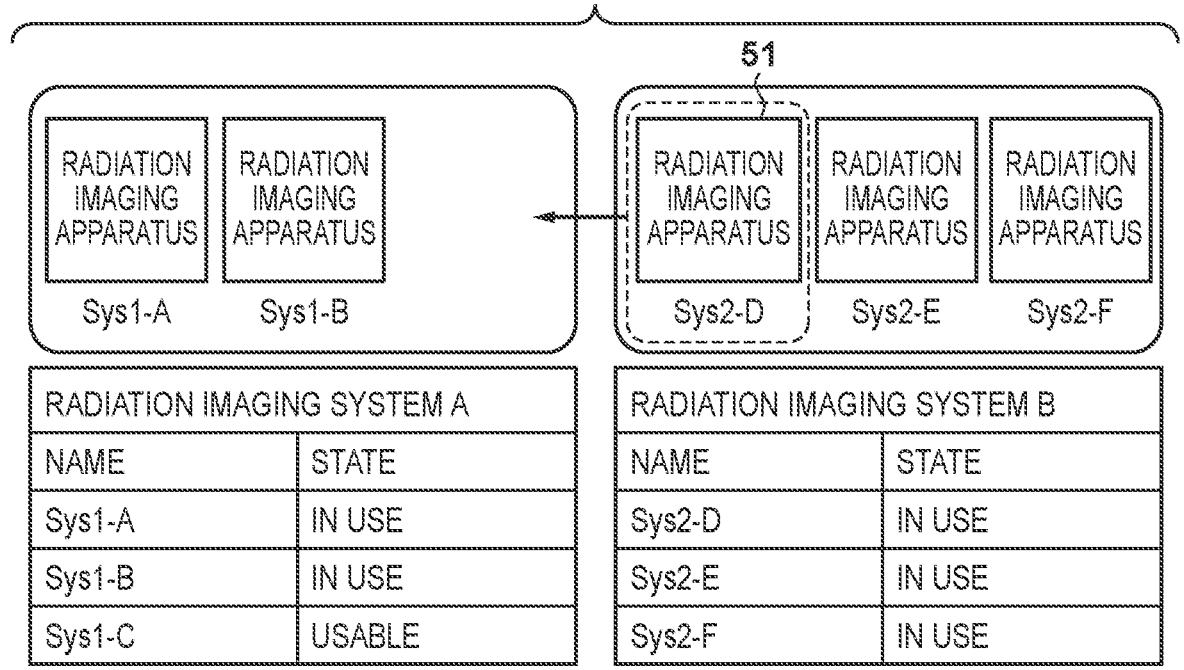
FIGS. 5A to 5D are schematic views showing a procedure of changing the name of a radiation imaging apparatus and examples of display of lists according to the first embodiment.
Figure 5B:
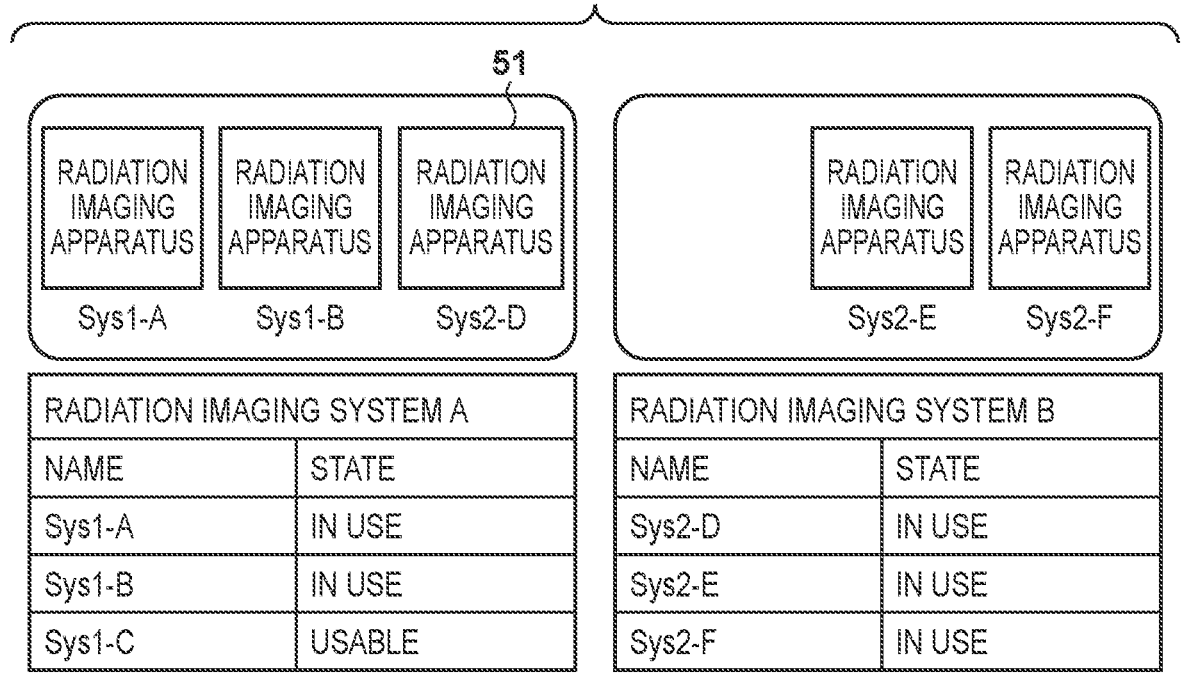
Figure 5C:
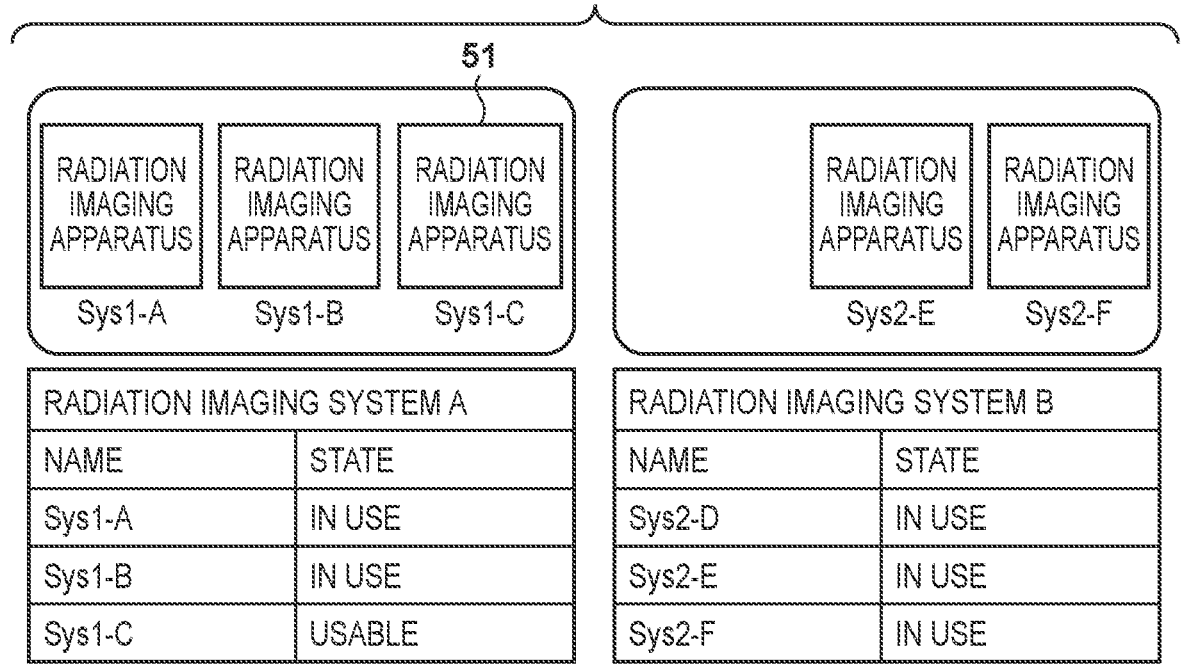

FIGS. 5A to 5D are schematic views showing a procedure of changing the name of a radiation imaging apparatus and examples of display of lists. As shown in FIG. 5A, a radiation imaging apparatus 51 used in the radiation imaging system B is assigned with the name (Sys2-D) of a radiation imaging apparatus usable in the radiation imaging system B. As shown in FIG. 5A, if the radiation imaging apparatus 51 used in the radiation imaging system B is carried to the other radiation imaging system A, and is made to cooperate with the control apparatus 5-1, a state shown in FIG. 5B is obtained. Then, if the control apparatus 5-1 assigns, among usable names, a name (Sys1-C), which is not currently used, to the radiation imaging apparatus 51 that has been carried from the radiation imaging system B to the radiation imaging system A, a state shown in FIG. 5C is obtained. That is, the name (Sys2-D) of the radiation imaging apparatus is changed to the name (Sys1-C) of the radiation imaging apparatus.

Figure 5D:
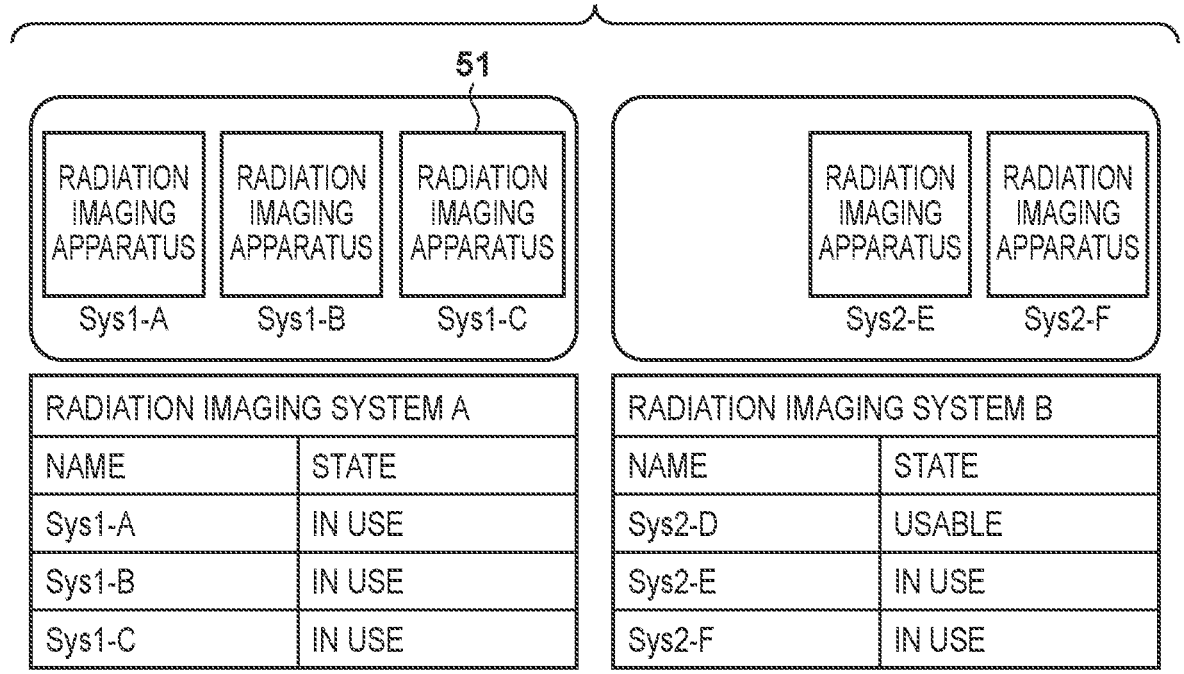

Finally, when the control apparatus 5-1 determines that the name of the radiation imaging apparatus 51 is usable in the radiation imaging system A, a state shown in FIG. 5D is obtained. The control apparatus 5-1 changes the state (status) of the radiation imaging apparatus having the name (Sys1-C) from "usable" to "in use". If the status of the radiation imaging apparatus having the name (Sys1-C) is changed from "usable" to "in use", cooperation between the control apparatus 5-2 of the radiation imaging system B and the radiation imaging apparatus 51 is canceled. If the control apparatus 5-2 confirms that cooperation between the control apparatus 5-2 and the radiation imaging apparatus 51 is canceled, the control apparatus 5-2 changes the status of the name (Sys2-D) used by the radiation imaging apparatus 51 in the radiation imaging system B from "in use" to "usable".

When setting a name in a radiation imaging apparatus carried from another radiation imaging system, the control apparatus may randomly assign a name or, if there are a plurality of usable names in a list, the control apparatus may assign the name to the radiation imaging apparatus from above or below.

Figure 6:
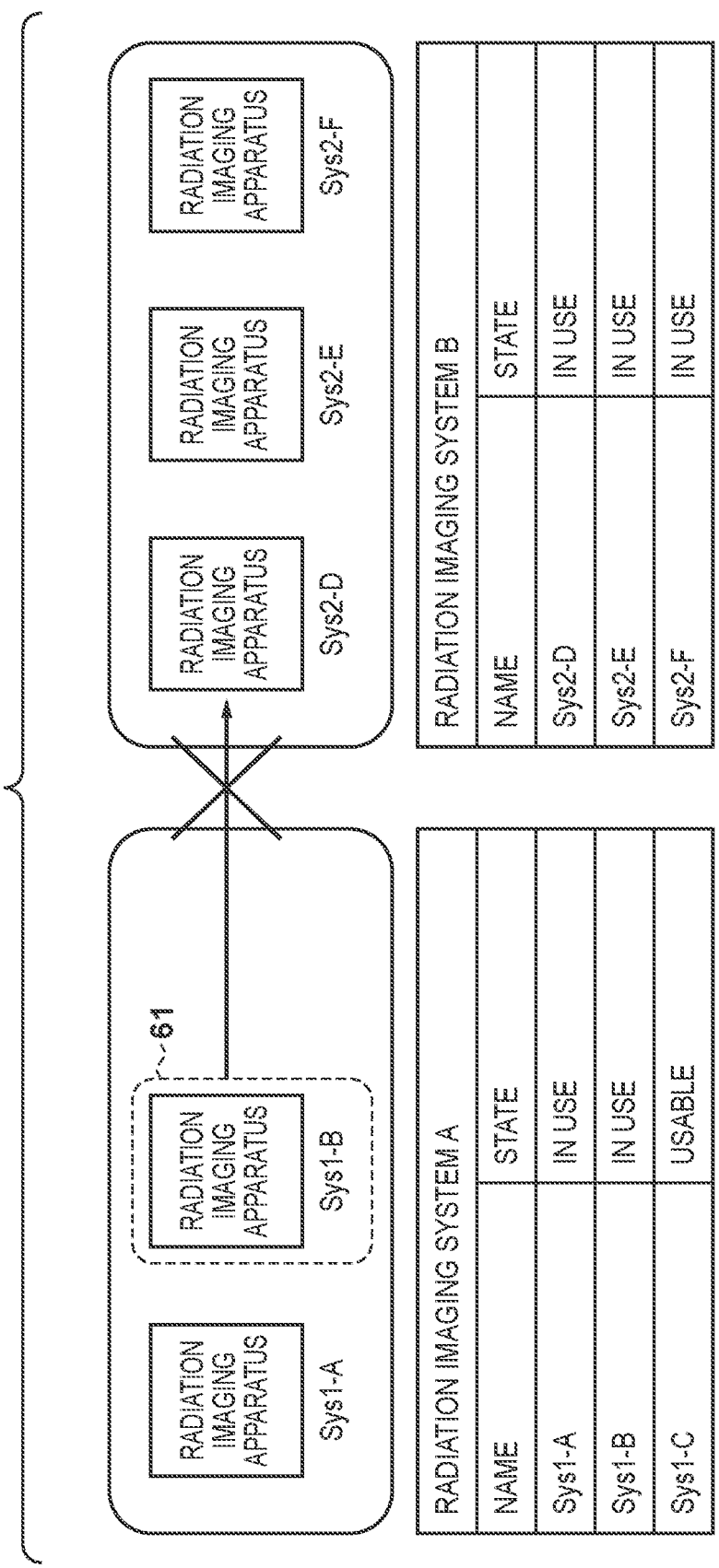
FIG. 6 is a schematic view when the name of a radiation imaging apparatus is not changed and shows an example of display of lists according to the first embodiment.

FIG. 6 is a schematic view when the name of a radiation imaging apparatus is not changed and shows an example of display of lists. As shown in FIG. 6, in the radiation imaging system B, all usable names are assigned to the radiation imaging apparatuses, and the statuses of all the radiation imaging apparatuses are "in use". If a radiation imaging apparatus 61 is carried from the radiation imaging system A to the radiation imaging system B, the control apparatus 5-2 determines that all the usable names are in use, and thus causes the radiation imaging apparatus 61 carried from the radiation imaging system A to the radiation imaging system B to maintain the current name (Sys1-B) assigned in the radiation imaging system A without assigning a name to the radiation imaging apparatus 61.

To clarify the fact that the name of the radiation imaging apparatus has been changed and made to cooperate with the radiation imaging system, the control apparatus displays the name of the radiation imaging apparatus cooperating with the radiation imaging system on the display unit 11 provided in the radiation imaging apparatus. With the name of the radiation imaging apparatus displayed on the display unit 11, the operator can determine the cooperative radiation imaging apparatus without confirming the control apparatus. Furthermore, if the name cannot be changed, the control apparatus displays an error on the display unit 11 to indicate, to the operator, that cooperation cannot be performed.

Figure 7:
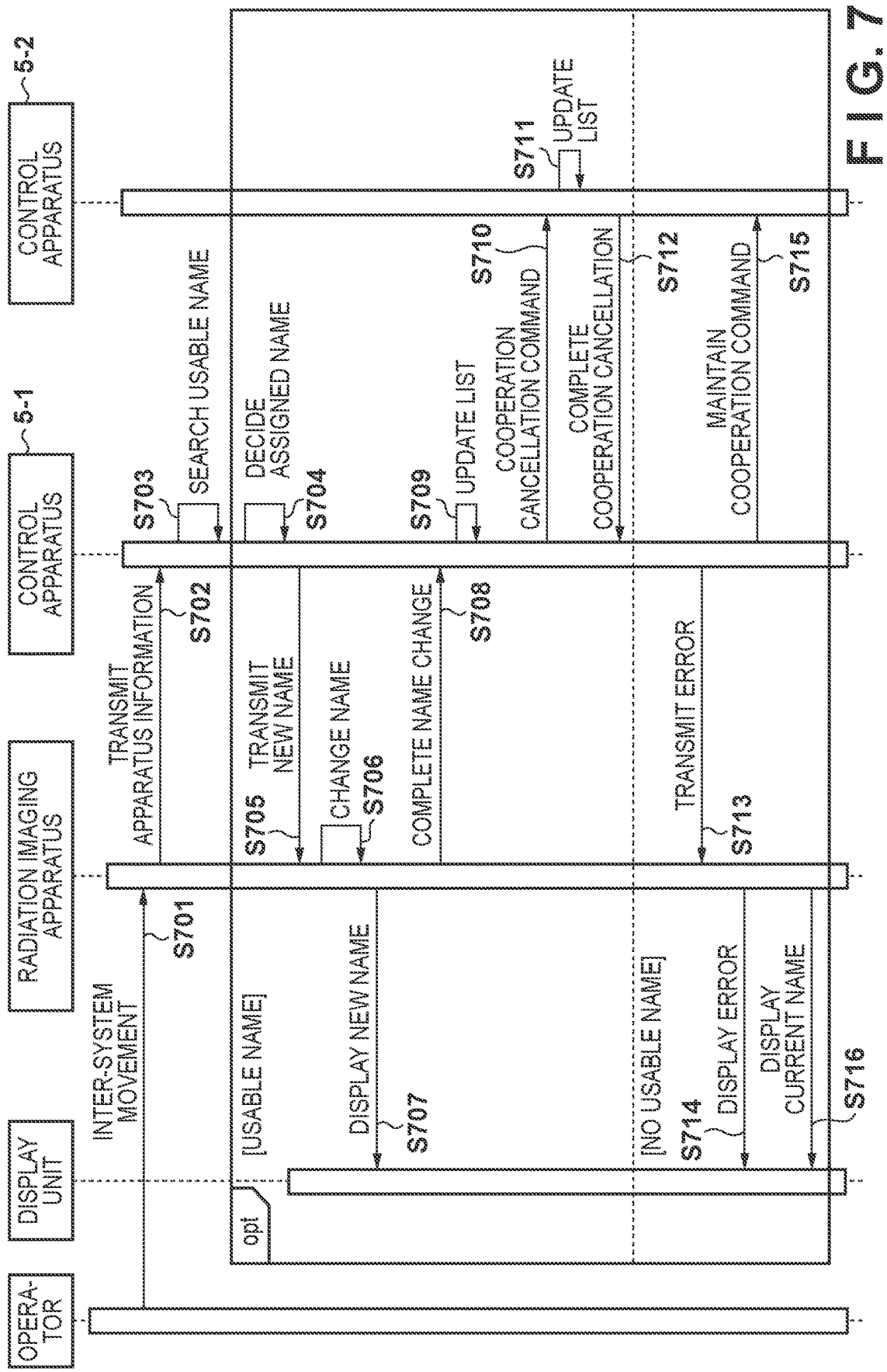
FIG. 7 is a sequence chart showing an operation of changing the name of the radiation imaging apparatus according to the first embodiment.

FIG. 7 is a sequence chart showing an operation of changing the name of a radiation imaging apparatus according to the first embodiment. If the operator performs inter-system movement of carrying a radiation imaging apparatus to another system (for example, from the radiation imaging system B to the radiation imaging system A in FIG. 1) (step S701), the radiation imaging apparatus transmits, to the control apparatus 5-1, apparatus information (name, size, and the like) as information for identifying an apparatus (step S702). Then, the control apparatus 5-1 searches for a name usable in the radiation imaging system A (step S703). The control apparatus 5-1 functions as a search unit that searches for apparatus information (name) usable in the radiation imaging system as a movement destination based on the transmitted apparatus information. The control apparatus 5-1 also functions as a decision unit that decides, based on a search result, a name to be assigned to the radiation imaging apparatus, and the control apparatus 5-1 transmits the decided name to the radiation imaging apparatus.

If the usable name is found, the control apparatus 5-1 decides a name to be assigned to the radiation imaging apparatus (step S704), and transmits the name to the radiation imaging apparatus (step S705). The control unit 21 (display control unit) of the radiation imaging apparatus controls display of the display unit 11 based on the name received from the control apparatus. The control unit 21 (display control unit) changes the set name to the name transmitted from the control apparatus 5-1 (step S706), and displays the changed new name on the display unit 11 provided in the radiation imaging apparatus (step S707).

The control apparatus includes a registration unit (list) that registers the apparatus information of the radiation imaging apparatus to cooperate by connection to the control apparatus 5-1 in the radiation imaging system as the movement destination of the radiation imaging apparatus. If, after completion of the change of the name, the control unit 21 (display control unit) of the radiation imaging apparatus transmits a signal indicating the completion of the change of the name to the control apparatus 5-1 via the wireless communication unit 27 (communication unit) (step S708), the control apparatus 5-1 executes update of the list (step S709).

The control apparatus 5-1 then transmits, to the other control apparatus 5-2 of the other radiation imaging system B as a movement source, to which the radiation imaging apparatus was connected, a command (cooperation cancellation command) to cancel cooperation with the radiation imaging apparatus (step S710). The other control apparatus 5-2 updates registration of the registration unit (list) of the other control apparatus 5-2 based on reception of the cooperation cancellation command (step S711), and transmits, to the control apparatus 5-1, cooperation cancellation completion as a signal for notifying the user of the completion of cooperation cancellation (step S712). With the above operation sequence, the name change processing of the radiation imaging apparatus moved between the systems is completed.

On the other hand, if there is no usable name at the time of inter-system movement, the control apparatus 5-1 transmits an error signal for notifying that there is no name usable for the radiation imaging apparatus (step S713), and the control unit 21 (display control unit) of the radiation imaging apparatus displays, on the display unit 11, error information for notifying that there is no usable name (step S714).

Then, the control apparatus 5-1 transmits, to the other control apparatus 5-2 of the other radiation imaging system B as a movement source, which cooperates with the radiation imaging apparatus in advance, a command to maintain cooperation with the radiation imaging apparatus (step S715), and the control unit 21 (display control unit) of the radiation imaging apparatus displays again, on the display unit 11, the name set in the radiation imaging apparatus (step S716). When a predetermined time (for example, several sec) elapses after the control apparatus 5-1 transmits, to the other control apparatus 5-2, the command to maintain cooperation with the radiation imaging apparatus, the control unit 21 (display control unit) of the radiation imaging apparatus displays again, on the display unit 11, the name set in the radiation imaging apparatus. With the above-described operation sequence in steps S713 to S716, the processing when there is no usable name for the radiation imaging apparatus moved between the systems is completed.

According to the first embodiment, when moving between the radiation imaging systems, the name of the radiation imaging apparatus is automatically changed to a name corresponding to the radiation imaging system as a movement destination, and the name can be displayed on the radiation imaging apparatus. Therefore, the operator can confirm that cooperation can be performed with a desired radiation imaging system by confirming the name displayed on the display unit of the radiation imaging apparatus, and an operation of confirming, in the control apparatus, whether cooperation between the radiation imaging apparatus and the radiation imaging system has been performed can be skipped.

Second Embodiment

The second embodiment will be described next. As an outline of the second embodiment, an arrangement in which if the name of a radiation imaging system is registered, names of radiation imaging apparatuses can be automatically generated without setting the names by a person will be described. FIGS. 8A to 8C are views showing examples of display of a list for automatically assigning names of radiation imaging apparatuses. FIGS. 8A to 8C each exemplify the screen of a control apparatus that makes it possible to automatically decide names to be assigned to radiation imaging apparatuses. The present invention, however, is not limited to this. Assume that a basic arrangement and a system structure of switching the name of a radiation imaging apparatus are the same as in the first embodiment.

Note that the same reference numerals as in the first embodiment denote similar constituent elements and a detailed description thereof will be omitted.

A control apparatus 5-1 or 5-2 automatically generates names of radiation imaging apparatuses based on the registered name of a radiation imaging system. The control apparatus 5-1 or 5-2 generates names of radiation imaging apparatuses based on a combination of the name of the radiation imaging system and a selection method selected by an operator, and a registration unit (list) of the control apparatus 5-1 or 5-2 registers the created names as pieces of apparatus information of the radiation imaging apparatuses.

In the control apparatus 5-1 or 5-2, a setting screen in which names can be set manually or automatically is provided in a name setting screen for the radiation imaging apparatuses. If "auto" is selected in the setting screen, automatic selection methods are distinguished by, for example, three kinds of methods of "serial number", "alphabet" (including an alphabet character or character string), and "original". If the selection method selected in the setting screen of the control apparatus 5-1 or 5-2 is "serial number", the control apparatus 5-1 or 5-2 generates a name of each radiation imaging apparatus by a combination of the name of the target radiation imaging system and a serial number. If "serial number" is selected as shown in FIG. 8A, a name like "Xray system1-001" or "Xray system1-002" is obtained by a combination of the name (Xray system1) of the target radiation imaging system and a serial number.

If the selection method selected in the setting screen of the control apparatus 5-1 or 5-2 is "alphabet", the control apparatus 5-1 or 5-2 generates a name of each radiation imaging apparatus by a combination of the name of the target radiation imaging system and an alphabet character. If "alphabet" is selected as shown in FIG. 8B, a name is set from A in combination with the name (Xray system1) of the target radiation imaging system, and a name like "Xray system1-A" or "Xray system1-B" is obtained.

If the selection method selected in the setting screen of the control apparatus 5-1 or 5-2 is "original", the control apparatus 5-1 or 5-2 generates a name of each radiation imaging apparatus by a combination of the name of the target radiation imaging system and a character set by the operator in the setting screen. If "original" is selected as shown in FIG. 8C, a name (for example, "alpha" or "beta") obtained by using an original character string set by the control apparatus in combination with the name (Xray system1) of the target radiation imaging system is set, and a name like "Xray system1-alpha" or "Xray system1-beta" is obtained. This original character string may be the name of the operator, a place name, a model name, or the like.

According to the second embodiment, a name corresponding to a system can be set automatically without considering a name corresponding to the system by the operator.

Third Embodiment

The third embodiment will be described next. As an outline of the third embodiment, an arrangement of setting, depending on the size of a radiation imaging apparatus, a name to be assigned to the radiation imaging apparatus will be described. FIG. 9 is a view showing an example of display of a list of radiation imaging apparatuses during cooperation in accordance with sizes. As shown in FIG. 9, a control apparatus assigns a name of Sys1-A or Sys1-B to a radiation imaging apparatus of a half size, and does not assign other names.

FIG. 9 exemplifies the screen of the control apparatus in which a name assigned to each radiation imaging apparatus is decided in accordance with the size of the radiation imaging apparatus. The present invention, however, is not limited to this. Assume that a basic arrangement and a system and operation of switching the name of a radiation imaging apparatus are the same as in the first embodiment. Note that the same reference numerals as in the first embodiment denote similar constituent elements and a detailed description thereof will be omitted.

A usable size can be individually set in the control apparatus, and each of the control apparatuses of radiation imaging systems can cooperate with a control apparatus in a hospital using a connected communication path 6 to detect all the sizes of the radiation imaging apparatuses used by each control apparatus. Note that it is unnecessary to set names for all the detected sizes, and a name may be set for a usable size for each radiation imaging system.

Figure 10A:
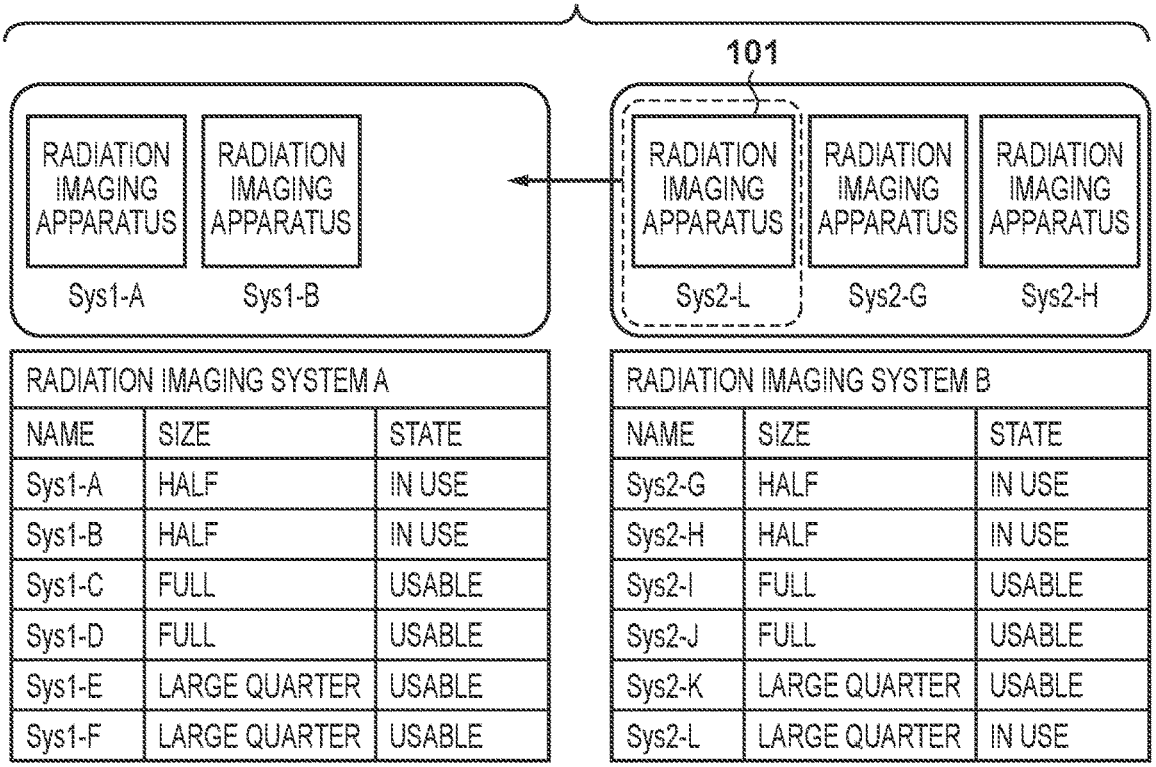
FIGS. 10A to 10D are schematic views showing a procedure of changing the name of a radiation imaging apparatus and examples of display of lists according to the third embodiment.
Figure 10B:
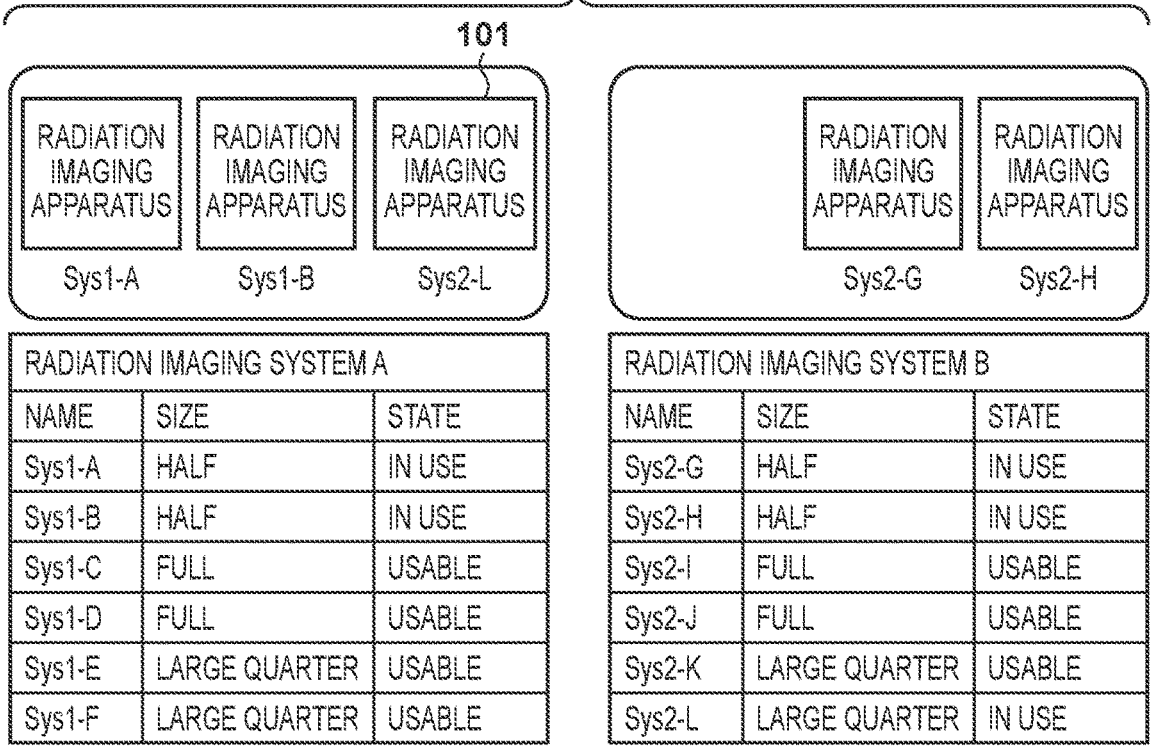

FIGS. 10A to 10D are schematic views showing a procedure of changing the name of a radiation imaging apparatus and examples of display of lists according to the third embodiment. As shown in FIG. 10A, a name (Sys2-L) of a radiation imaging apparatus usable in a radiation imaging system B is assigned to a radiation imaging apparatus 101 of a large quarter size used in the radiation imaging system B. If the radiation imaging apparatus 101 used in the radiation imaging system B is carried to another radiation imaging system A, as shown in FIG. 10A, a state shown in FIG. 10B is obtained.

Figure 10C:
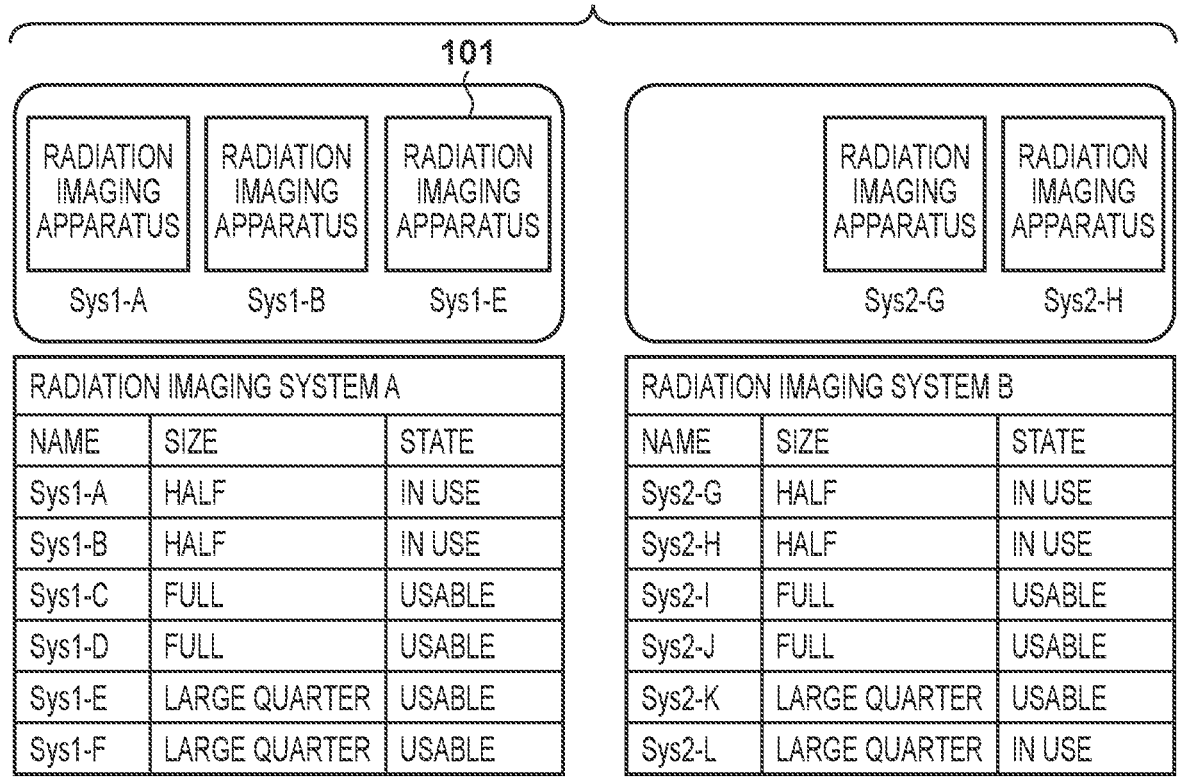

If a control apparatus 5-1 of the radiation imaging system A assigns, among usable names of the large quarter size, a name (Sys1-E), which is not currently used, to the radiation imaging apparatus 101 carried from the radiation imaging system B to the radiation imaging system A, a state shown in FIG. 10C is obtained. That is, the name (Sys2-L) of the radiation imaging apparatus is changed to the name (Sys1-E) of the radiation imaging apparatus.

Figure 10D:
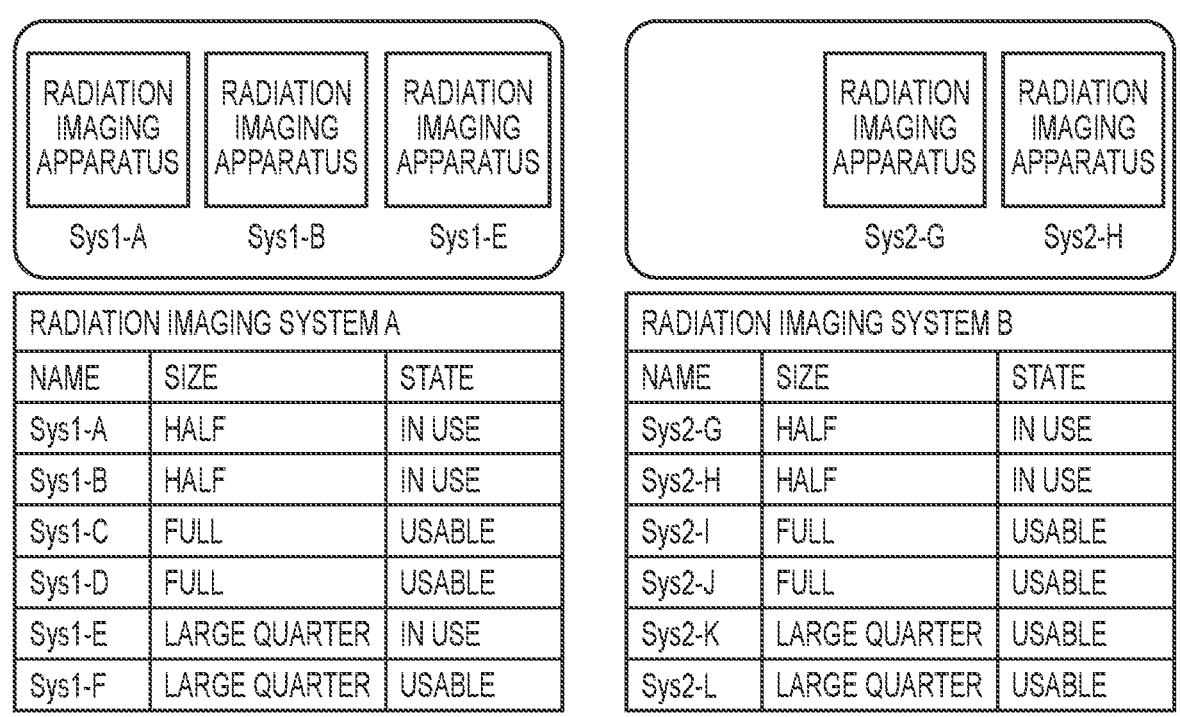

Finally, if the control apparatus 5-1 determines that the name of the radiation imaging apparatus 101 is usable in the radiation imaging system A, a state shown in FIG. 10D is obtained. The control apparatus 5-1 changes the state (status) of the radiation imaging apparatus having the name (Sys1-E) from "usable" to "in use". If the status of the radiation imaging apparatus having the name (Sys1-E) is changed from "usable" to "in use", cooperation between the radiation imaging apparatus 101 and a control apparatus 5-2 of the radiation imaging system B is canceled. If the control apparatus 5-2 confirms that cooperation between the radiation imaging apparatus 101 and the control apparatus 5-2 is canceled, the control apparatus 5-2 changes the status of the name (Sys2-L) used by the radiation imaging apparatus 101 from "in use" to "usable".

Figure 11:
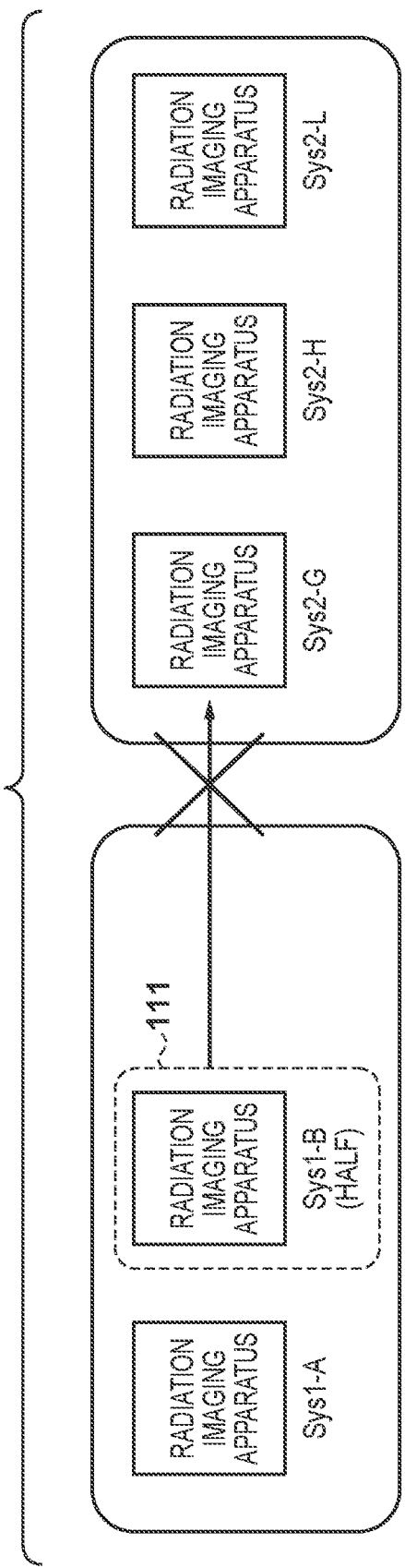
FIG. 11 is a schematic view and an example of display of lists when the name of a radiation imaging apparatus is not changed according to the third embodiment.

FIG. 11 is a schematic view and an example of display of lists when the name of a radiation imaging apparatus is not changed according to the third embodiment. As shown in FIG. 11, if a radiation imaging apparatus 111 (Sys-B) of a half size used in the radiation imaging system A is carried to the radiation imaging system B, the control apparatus 5-2 determines that all usable names of the half size are in use, and thus causes the radiation imaging apparatus 111 carried from the radiation imaging system A to the radiation imaging system B to maintain the current name (Sys1-B) assigned in the radiation imaging system A without assigning a name to the radiation imaging apparatus 111.

Figure 12:
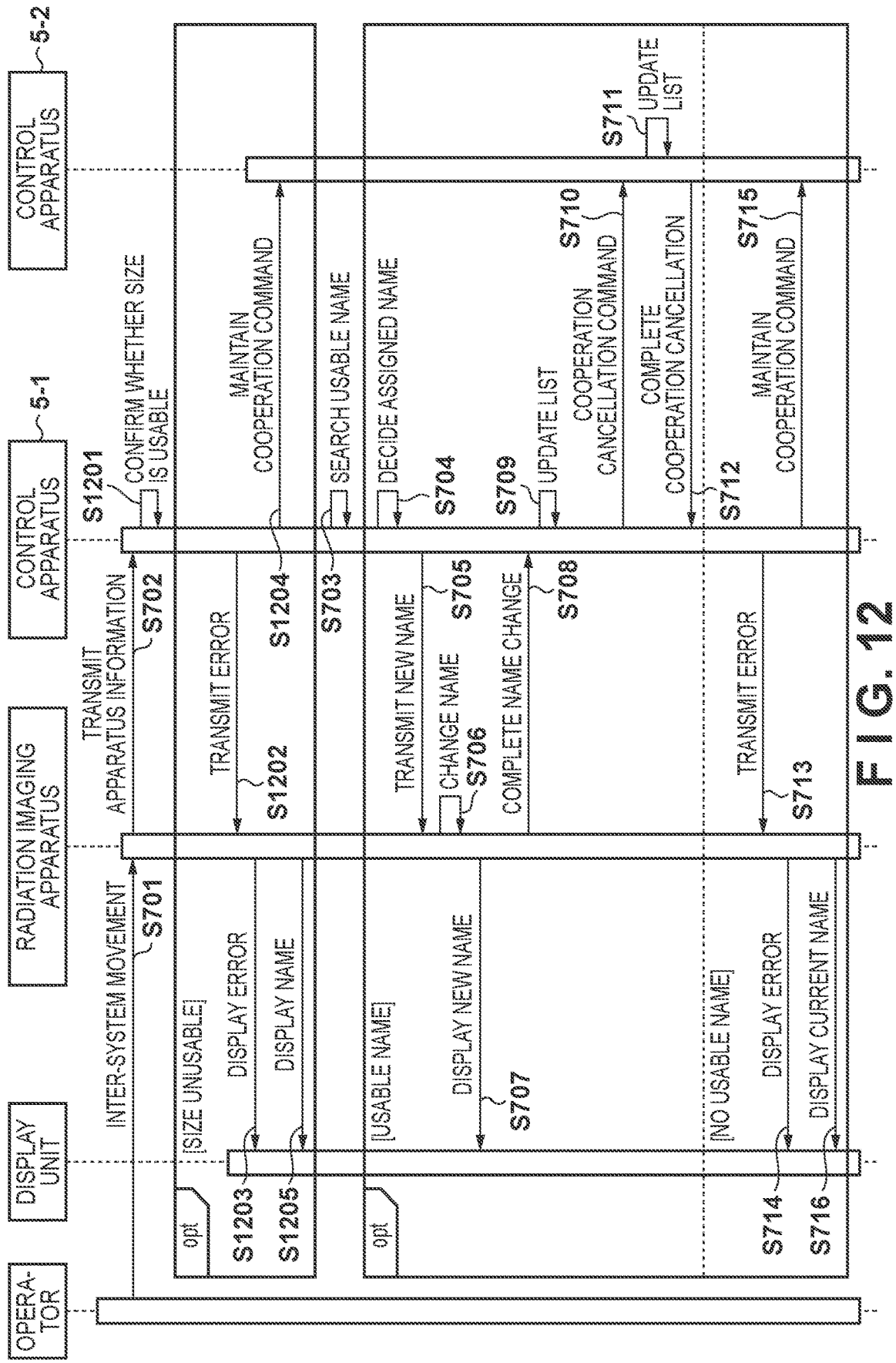
FIG. 12 is a sequence chart showing an operation of changing the name of the radiation imaging apparatus according to the third embodiment.

FIG. 12 is a sequence chart showing an operation of changing the name of the radiation imaging apparatus according to the third embodiment. Steps S701 to S715 are the same as in FIG. 7 and a difference will be described. After, in step S702, the radiation imaging apparatus transmits, to the control apparatus 5-1, apparatus information (name, size, and the like) as information for identifying an apparatus, the control apparatus 5-1 confirms whether the size of the radiation imaging apparatus is usable in the radiation imaging system (step S1201).

If the size of the radiation imaging apparatus is unusable, the control apparatus 5-1 transmits, to the radiation imaging apparatus, an error signal for notifying that there is no usable size (step S1202), and a control unit 21 (display control unit) of the radiation imaging apparatus displays, on a display unit 11, error information for notifying that there is no usable size (step S1203). Then, the control apparatus 5-1 transmits, to the other control apparatus 5-2 of the other radiation imaging system B as a movement source, which cooperates with the radiation imaging apparatus in advance, a command to maintain cooperation with the radiation imaging apparatus (step S1204). When a predetermined time (for example, several sec) elapses after the control apparatus 5-1 transmits, to the other control apparatus 5-2, the command to maintain cooperation with the radiation imaging apparatus, the control unit 21 (display control unit) of the radiation imaging apparatus displays the name again on the display unit 11 (step S1205).

If the size of the radiation imaging apparatus is usable, step S703 and subsequent steps are executed. An operation sequence in step S703 and the subsequent steps is the same as in FIG. 7, and a description thereof will be omitted.

In addition to the change of the name of the radiation imaging apparatus in movement between the radiation imaging systems, the present invention is applicable at the time of additionally introducing or replacing a radiation imaging apparatus. At the time of additionally introducing or replacing a radiation imaging apparatus, processes similar to those in steps S701 and S702 are executed. An imaging protocol including at least one of pieces of information concerning an imaging part and an imaging table for imaging, image processing, an imaging condition, and the like is transferred when specifications such as the size of the radiation imaging apparatus and a sensor type are common. Then, after calibration (correction based on a dark image, a gain image, a defective pixel, or the like) of the radiation imaging apparatus is performed and individual characteristics of the radiation imaging apparatus are acquired, actual imaging becomes possible.

According to the third embodiment, it is possible to automatically assign a name in consideration of the size of a radiation imaging apparatus, and set a usable size for each radiation imaging system, thereby making it possible to operate radiation imaging systems by setting application purposes.

As described above, in the system that automatically changes the name of a radiation imaging apparatus when moving between the radiation imaging systems, the name of the radiation imaging apparatus is automatically changed to a name corresponding to the radiation imaging system, and cooperation with the radiation imaging system is automatically performed. Since it is known, by confirming the radiation imaging apparatus, that cooperation has been performed, the work efficiency is improved. That is, the operator can confirm, by confirming the name displayed on the display unit of the radiation imaging apparatus, that cooperation with a desired radiation imaging system has been performed, and it is possible to eliminate a work of confirming, in the control apparatus, whether cooperation between the radiation imaging apparatus and the radiation imaging system has been performed.

According to the embodiments of the present invention, it is possible to associate the name of a radiation imaging apparatus with a radiation imaging system, and the operator can know, by viewing the radiation imaging apparatus, whether cooperation between the radiation imaging apparatus and the radiation imaging system has been performed. Therefore, it is possible to confirm, without viewing the control apparatus, whether cooperation between the radiation imaging apparatus and the radiation imaging system has been performed, thereby providing a radiation imaging technique capable of improving the usability of the operator.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-209002, filed Nov. 19, 2019, which is hereby incorporated by reference herein in its entirety.

What is claimed is:

1. A radiation imaging system comprising a radiation imaging apparatus configured to detect radiation and generate radiation image data and a control apparatus configured to communicate with the radiation imaging apparatus,
wherein the radiation imaging apparatus comprises
a radiation detector;
a first communication unit configured to transmit apparatus information for identifying an apparatus to the control apparatus as a movement destination,
a display unit configured to display a name of the radiation imaging apparatus, and
a display controller configured to control the display unit,
wherein the control apparatus comprises a processor coupled to a storage medium and programmed to function as:
a search unit configured to search for apparatus information usable in the radiation imaging system as the movement destination based on the transmitted apparatus information,
a decision unit configured to change, based on a result of the search, a name to be assigned to the radiation imaging apparatus, and
a second communication unit configured to transmit the changed name to the radiation imaging apparatus, and
wherein the display controller controls the display unit to display the changed name.

2. The system according to claim 1, wherein the apparatus information includes the name of the radiation imaging apparatus or a name set depending on a size of the radiation imaging apparatus.

3. The system according to claim 1, wherein the processor is programmed to further function as a registration unit configured to register the apparatus information of the radiation imaging apparatus to cooperate by connection to the control apparatus in the radiation imaging system as the movement destination.

4. The system according to claim 3, wherein
if the search unit finds a name usable as the apparatus information, the second communication unit transmits the decided name to the radiation imaging apparatus, and
the display controller changes the set name to the name transmitted from the control apparatus, and displays the changed name on the display unit.

5. The system according to claim 4, wherein
after completion of the change of the name, the display controller transmits a signal indicating name change completion to the control apparatus via the first communication unit, and
the registration unit updates the registration of the apparatus information based on reception of the name change completion.

6. The system according to claim 5, wherein the second communication unit transmits, to another control apparatus of another radiation imaging system as a movement source, to which the radiation imaging apparatus was connected, a cooperation cancellation command to cancel cooperation with the radiation imaging apparatus.

7. The system according to claim 6, wherein the other control apparatus updates registration of the registration unit of the other control apparatus based on reception of the cooperation cancellation command, and transmits, to the control apparatus, a signal for notifying that cooperation cancellation is complete.

8. The system according to claim 3, wherein
if the search unit does not find a name usable as the apparatus information, the second communication unit transmits, to the radiation imaging apparatus, an error signal for notifying that there is no usable name, and
the display controller displays, on the display unit, error information for notifying that there is no usable name.

9. The system according to claim 8, wherein
the second communication unit transmits, to another control apparatus of another radiation imaging system as a movement source, which cooperates with the radiation imaging apparatus in advance, a command to maintain cooperation with the radiation imaging apparatus, and the display controller displays again, on the display unit, the name set in the radiation imaging apparatus.

10. The system according to claim 3, wherein
the processor is programmed to further function as a generation unit configured to automatically generate a name of the radiation imaging apparatus based on a registered name of the radiation imaging system,
the generation unit generates the name of the radiation imaging apparatus based on a combination of the name of the radiation imaging system and a selection method selected by an operator, and
the registration unit registers, as the apparatus information of the radiation imaging apparatus, the generated name.

11. The system according to claim 10, wherein if the selection method selected in a setting screen of the control apparatus is a serial number, the generation unit generates the name of the radiation imaging apparatus by a combination of the name of the target radiation imaging system and a serial number.

12. The system according to claim 10, wherein if the selection method selected in a setting screen of the control apparatus is an alphabet, the generation unit generates the name of the radiation imaging apparatus by a combination of the name of the target radiation imaging system and an alphabet character.

13. The system according to claim 10, wherein if the selection method selected in a setting screen of the control apparatus is an original character, the generation unit generates the name of the radiation imaging apparatus by a combination of the name of the target radiation imaging system and a character set by the operator in the setting screen.

14. The system according to claim 3, wherein
if the search unit determines that a size of the radiation imaging apparatus is unusable as the apparatus information, the second communication unit transmits, to the radiation imaging apparatus, an error signal for notifying that there is no usable size, and
the display controller displays, on the display unit, error information for notifying that there is no usable size.

15. The system according to claim 14, wherein
the second communication unit transmits, to another control apparatus of another radiation imaging system as a movement source, which cooperates with the radiation imaging apparatus in advance, a command to maintain cooperation with the radiation imaging apparatus, and
the display controller displays again, on the display unit, the name set in the radiation imaging apparatus.

16. A radiation imaging apparatus, comprising:
a radiation detector;
a communication unit configured to transmit apparatus information for identifying an apparatus to a control apparatus of a radiation imaging system as a movement destination;
a display unit configured to display a name of the radiation imaging apparatus; and
a display controller configured to control the display unit,
wherein the control apparatus searches for apparatus information usable in the radiation imaging system as the movement destination based on the apparatus information, and changes, based on a result of the search, a name to be assigned to the radiation imaging apparatus, and
the display controller controls the display unit to display the changed name.

17. A control method for radiation imaging systems comprising a radiation imaging apparatus configured to detect radiation and generate radiation image data and a control apparatus configured to communicate with the radiation imaging apparatus, the method comprising:
in the radiation imaging apparatus,
transmitting apparatus information for identifying an apparatus to the control apparatus of the radiation imaging system as a movement destination,
displaying, on a display unit, a name of the radiation imaging apparatus, and
controlling the display unit;
in the control apparatus,
searching for apparatus information usable in the radiation imaging system as the movement destination based on the transmitted apparatus information,
changing, based on a result of the search, a name to be assigned to the radiation imaging apparatus, and
transmitting the changed name to the radiation imaging apparatus; and
in the radiation imaging apparatus,
controlling the display unit to display the received name.

18. The control method according to claim 17, wherein the apparatus information includes the name of the radiation imaging apparatus or a name set depending on a size of the radiation imaging apparatus.

19. The control method according to claim 17, further comprising registering the apparatus information of the radiation imaging apparatus to cooperate by connection to the control apparatus in the radiation imaging system as the movement destination.

20. The control method according to claim 19, further comprising:
transmitting the decided name to the radiation imaging apparatus, if the searching finds a name usable as the apparatus information;
changing the set name to the transmitted name; and
displaying the changed name on the display unit.

* * * * *